(12) United States Patent
Walker et al.

(10) Patent No.: US 11,931,265 B2
(45) Date of Patent: Mar. 19, 2024

(54) EXPANDABLE ORTHOPEDIC IMPLANT

(71) Applicant: Zavation, LLC, Flowood, MS (US)

(72) Inventors: John Lawrence Walker, Madison, MS (US); Joseph Matthew Jones, Madison, MS (US)

(73) Assignee: Zavation, LLC, Flowood, MS (US)

( * ) Notice: Subject to any disclaimer, the term of this patent is extended or adjusted under 35 U.S.C. 154(b) by 347 days.

(21) Appl. No.: 17/351,780

(22) Filed: Jun. 18, 2021

(65) Prior Publication Data

US 2021/0307920 A1 Oct. 7, 2021

Related U.S. Application Data

(63) Continuation of application No. 16/360,298, filed on Mar. 21, 2019, now Pat. No. 11,051,949, which is a continuation of application No. 16/135,734, filed on Sep. 19, 2018, now Pat. No. 10,278,830.

(60) Provisional application No. 62/627,326, filed on Feb. 7, 2018.

(51) Int. Cl.
*A61F 2/44* (2006.01)
*A61F 2/46* (2006.01)
*A61F 2/28* (2006.01)
*A61F 2/30* (2006.01)

(52) U.S. Cl.
CPC ............ *A61F 2/442* (2013.01); *A61F 2/4455* (2013.01); *A61F 2/447* (2013.01); *A61F 2/4611* (2013.01); *A61F 2002/2835* (2013.01); *A61F 2002/30387* (2013.01); *A61F 2002/30405* (2013.01); *A61F 2002/30507* (2013.01); *A61F 2002/30515* (2013.01); *A61F 2002/30556* (2013.01); *A61F 2002/30579* (2013.01); *A61F 2002/30593* (2013.01); *A61F 2002/30904* (2013.01); *A61F 2220/0025* (2013.01); *A61F 2310/00023* (2013.01)

(58) Field of Classification Search
CPC .. A61F 2/44; A61F 2/442; A61F 2/447; A61F 2/4455; A61F 2/46; A61F 2/4611
See application file for complete search history.

(56) References Cited

U.S. PATENT DOCUMENTS

| 11,051,949 B2* | 7/2021 | Walker | A61F 2/447 |
| 2014/0180421 A1* | 6/2014 | Glerum | A61F 2/447 623/17.16 |
| 2014/0243982 A1* | 8/2014 | Miller | A61F 2/447 623/17.16 |

* cited by examiner

*Primary Examiner* — Christopher J Beccia
(74) *Attorney, Agent, or Firm* — IP & T GROUP LLP

(57) ABSTRACT

An expandable intervertebral implant having an upper body portion, a lower body portion opposite the upper body portion. a wedge member connecting the upper body portion to the lower body portion, a nose member having a tapered distal end and a proximal end opposite the distal end, and an actuator disposed between the nose member and the wedge member, for translation of the wedge member along a longitudinal axis of the implant. A pin disposed in a center of the nose member connects to the actuator for centering the nose member with the actuator. Translation of the wedge member along the longitudinal axis of the implant displaces the upper body portion and the lower body portion away from each other, thereby expanding the intervertebral implant.

20 Claims, 7 Drawing Sheets

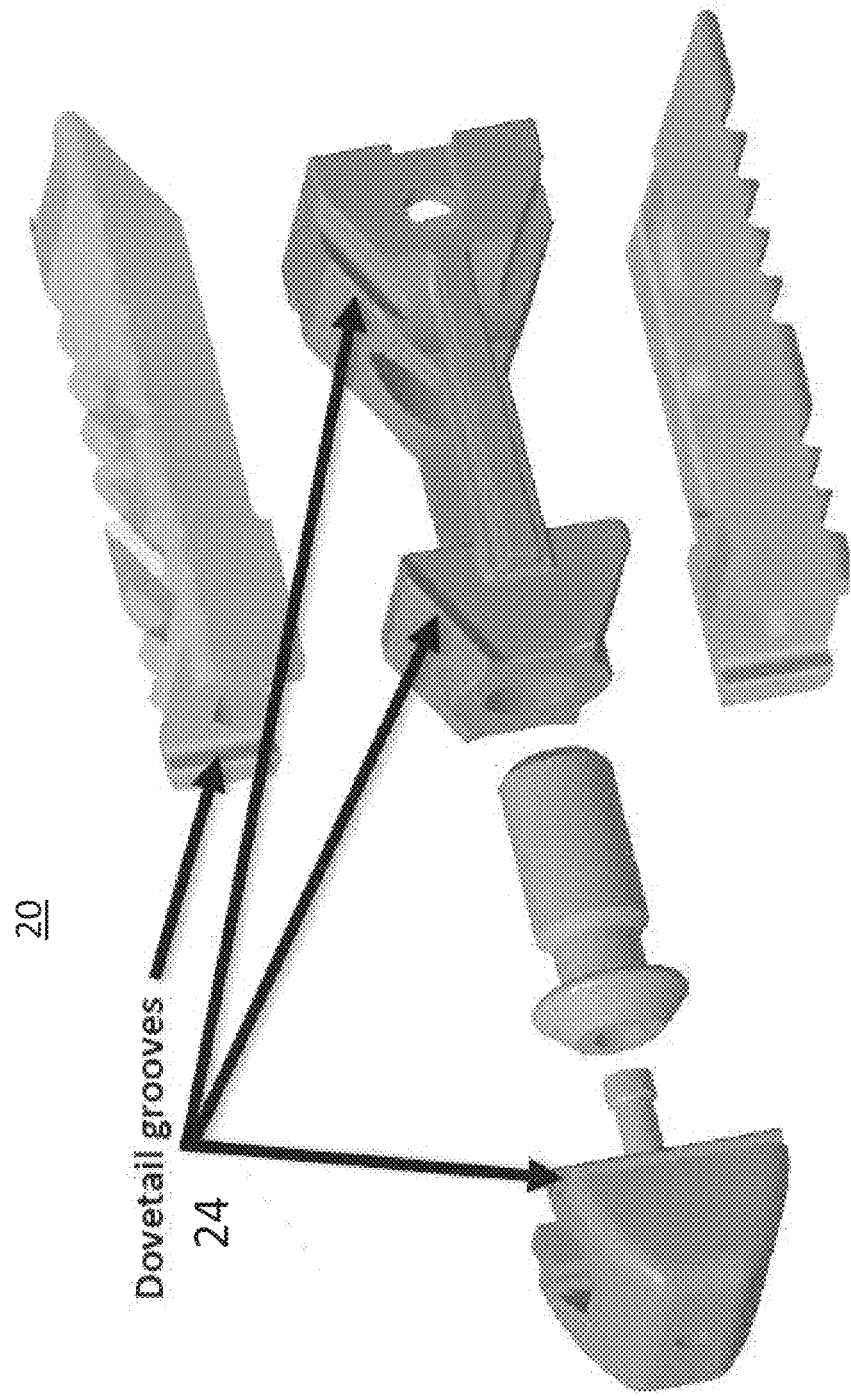

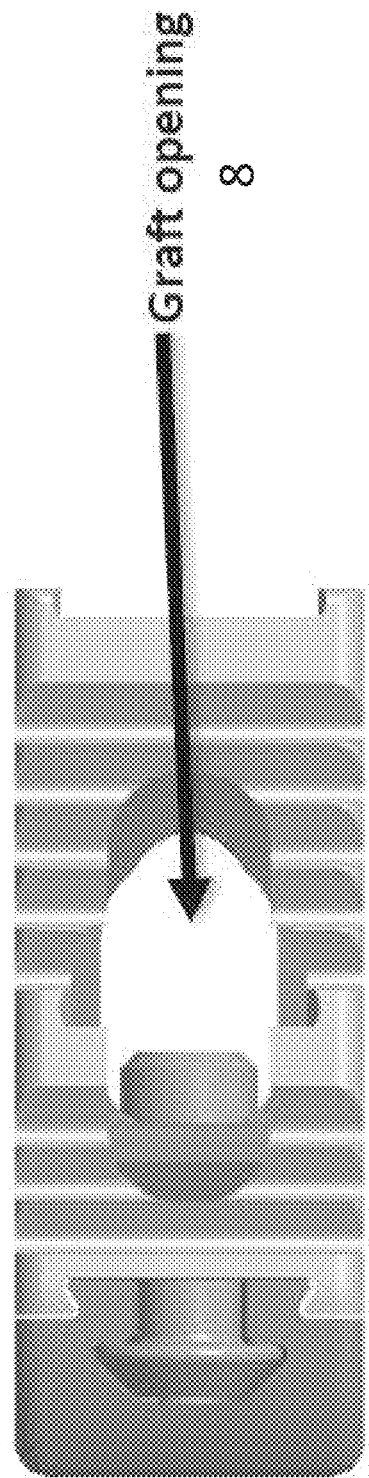

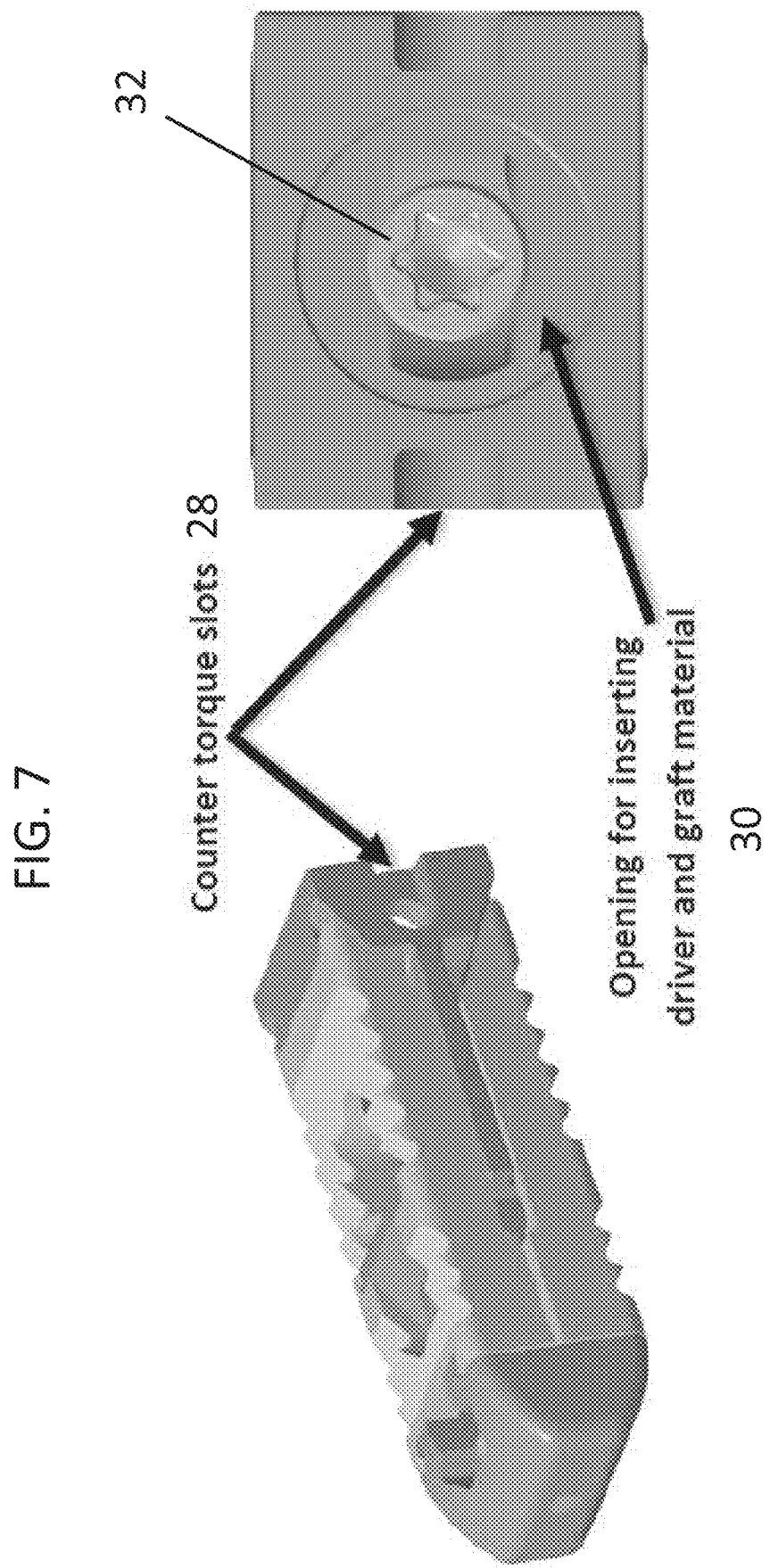

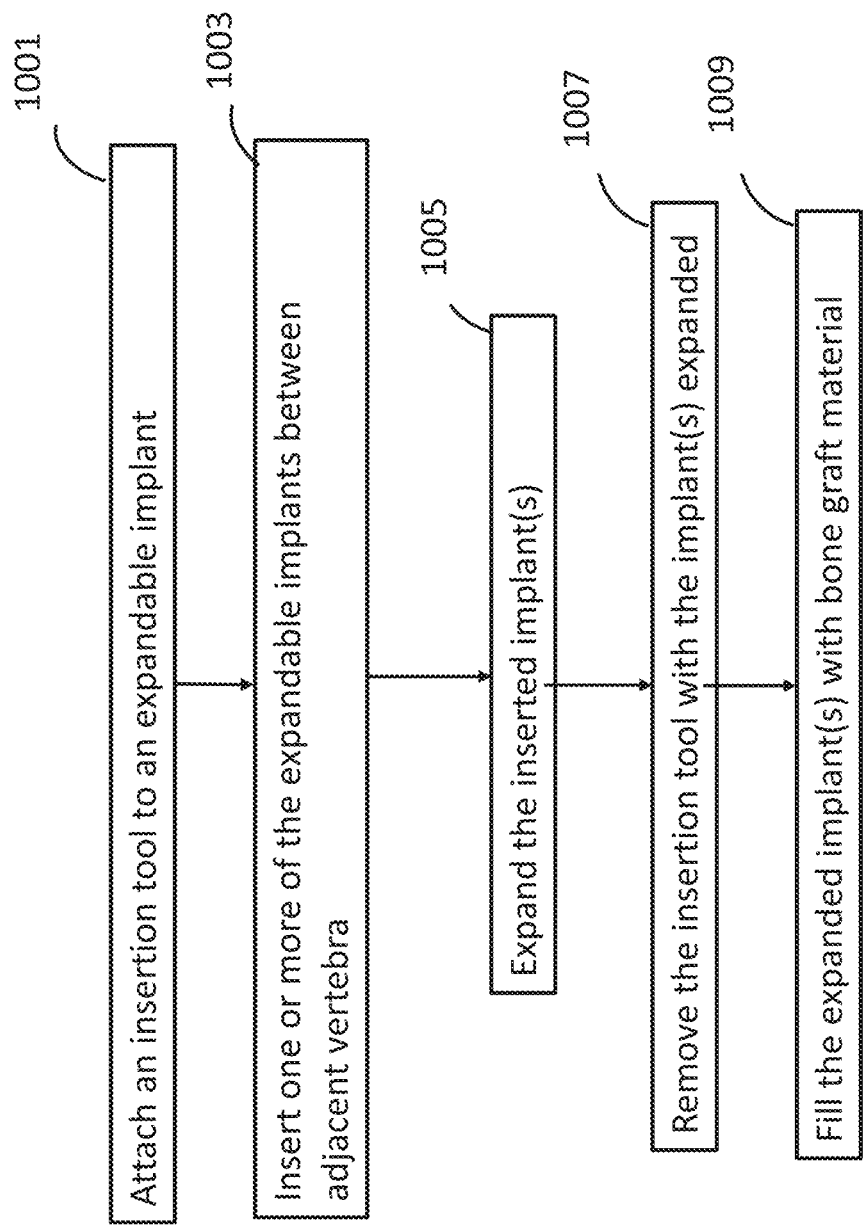

EXPANDABLE ORTHOPEDIC IMPLANT

CROSS REFERENCE TO RELATED APPLICATIONS

This application is a continuation application of U.S. Ser. No. 16/360,298 filed Mar. 21, 2019 which is a continuation of U.S. Ser. No. 16/135,734 filed Sep. 19, 2018. which is related and claims priority to U.S. Ser. No. 62/627,326, entitled Expandable Orthopedic Implant. filed Feb. 7, 2018, the entire contents of these applications are incorporated herein by reference.

BACKGROUND OF THE INVENTION

Field of the Invention

The present invention relates to implant devices for treating in particular spinal disorders.

Description of the Related Art

Disorders of the spine often result in degeneration of the spinal disc in the intervertebral space between the vertebral bodies. Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Conservative treatment can include non-operative treatment requiring patients to adjust their lifestyles and submit to pain relievers and a level of underlying pain. Operative treatment options include disc removal or the fusion or fixation of vertebrae together. Adjacent vertebra can be fixated or fused to each other using devices or bone grafts. These may include, for example, screw and rod systems, interbody spacers threaded fusion cages and the like.

Some fixation or fusion devices are attached to the vertebra from the posterior side. The device will protrude and result in additional length (i.e., needed to overlap the vertebrae) and additional hardware to separately attach to each vertebrae. Fusion cages and allografts are contained within the intervertebral space. but are inserted into the intervertebral space in the same dimensions as desired to occupy the intervertebral space. This requires that an opening sufficient to allow the cage or graft to be inserted into the intervertebral space.

In the field of medical implant devices, implant devices are often implanted into an intervertebral disc space in a collapsed state and expanded to a desired height. Expansion has been accomplished by translating an expansion mechanism mated to the inferior and superior endplates. In addition, a large aperture at the proximal end of the device allows for post packing of bone graft material into the hollow interior of the device, which is in communication with a fusion aperture in each of the superior and inferior endplates.

To achieve expansion and contraction the endplates are typically fixed in the longitudinal direction during translation of the expansion mechanism. An endplate retainer can be housed within the distal end of the housing mates with both the superior and inferior endplates and prohibits translation of the endplates. but allows for expansion.

U.S. Pat. No. 8,535,380 (the entire contents of which are incorporated herein by reference) describes an implantable orthopedic stability device. The device had a contracted and an expanded configuration which could support and be fixed to either or both of adjacent vertebrae.

U.S. Pat. No. 8,894,712 (the entire contents of which are incorporated herein by reference) describes an expandable intervertebral implant. including: a superior member configured to engage a superior intervertebral body; an inferior member configured to engage an inferior intervertebral body; and an expansion mechanism disposed between the superior member and the inferior member configured to selectively adjust a separation of the superior member from the inferior member.

U.S. Pat. No. 8,679,183 (the entire contents of which are incorporated herein by reference) describes an expandable fusion device capable of being installed inside an intervertebral disc space to maintain normal disc spacing and restore spinal stability. In the '183 patent. the fusion device includes a body portion, a first endplate, and a second endplate, the first and second endplates capable of being moved in a direction away from the body portion into an expanded configuration or capable of being moved towards the body portion into an unexpanded configuration.

U.S. Pat. No. 9,320,610 (the entire contents of which are incorporated herein by reference) describes an expandable implant including top and bottom plates having angled inner surface that interact with expansion members. The expansion members were situated on an actuator and included at least one vertical projection for interacting with a recess in the plates.

U.S. Pat. No. 9,414,936 (the entire contents of which are incorporated herein by reference) describes an intervertebral implant comprising a first component and a second component. The second component included an actuator and a third component comprises a first ramp and a second ramp axially spaced apart from the first ramp. The third component comprised rails including at least a portion of the ramps. The actuator was engageable with the third component to effect axial translation such that the ramps engage at least one of the components between a first configuration and a second configuration.

U.S. Pat. No. 9,526,627 (the entire contents of which are incorporated herein by reference) describes an intervertebral implant to be implanted within an intervertebral space between endplates of adjacent vertebra during use. The implant of the '627 patent included an upper member having an inferior surface including an upper guide track and a superior surface to contact an endplate of an upper one of the adjacent vertebra during use, a lower member having a superior surface including a lower guide track and an inferior surface to contact an endplate of a lower one of the adjacent vertebra during use. and an insert having a superior surface including an upper guide rail to engage the upper guide track during use and an inferior surface including a lower guide rail to engage the lower guide track during use.

U.S. Pat. No. 9,717,601 (the entire contents of which are incorporated herein by reference) describes an implant including a first plate and a second plate. a first wedge member and a second wedge member spaced from the first wedge member that couple the first and second plates together. In the '601 patent. the first and second wedge members were configured to translate along the first and second plates from a first contracted configuration into a second separated configuration. The implant included an actuation member coupled to the first wedge member and the second wedge member. The actuation member was configured to move the first and second wedge members from the first contracted configuration into the second separated configuration so that the first and second plates separate from each other.

U.S. Pat. No. 9,717,605 (the entire contents of which are incorporated herein by reference) describes a spinal fusion device that is expandable. The spinal fusion device of the '605 patent features a top and bottom surface for engaging adjacent vertebrae, a hollow center for stacking of bone or bone growth material, and a slidable mechanism with grooves for expanding or unexpanding the device.

U.S. Pat. No. 9,770,343 (the entire contents of which are incorporated herein by reference) describes a spacer for separating bones of a joint, the spacer includes a frame having a longitudinal axis. and ramped surfaces. In the '343 patent. an endplate configured to engage a bone of the joint had ramped surfaces mate-able with the ramped surfaces of the frame. When the endplate was moved relative to the frame in a direction along the longitudinal axis of the frame, the endplate was moved in a direction away from the frame to increase the height of the spacer.

U.S. Pat. No. 9,788,971 (the entire contents of which are incorporated herein by reference) describes an expandable spinal fusion implant comprising first and second endplates coupled to an expansion member that sits within a housing. The expansion member was translated by a drive mechanism, whereby translation of the expansion member by the drive mechanism in a distal and proximal directions caused the distance between the endplates to increase and decrease, respectively.

SUMMARY OF THE INVENTION

In one embodiment, there is provided an expandable intervertebral implant comprising an upper body portion. a lower body portion opposite the upper body portion. a wedge member connecting the upper body portion to the lower body portion, a nose member having a tapered distal end and a proximal end opposite the distal end, the nose member slidably connected to the upper body portion and the lower body portion, an actuator disposed between the nose member and the wedge member, for translation of the wedge member along a longitudinal axis of the implant, the actuator on a first side slidably connected the nose member and on a second side connected to the wedge member, and a pin disposed in a center of the nose member and connecting to the actuator for centering the nose member with the actuator. Translation of the wedge member along the longitudinal axis of the implant displaces the upper body portion and the lower body portion away from each other. thereby expanding the intervertebral implant.

In one embodiment, there is provided an expandable intervertebral implant comprising an upper body portion. a lower body portion opposite the upper body portion, a nose member having a tapered distal end and a proximal end opposite the distal end, a wedge member connecting the upper body portion to the lower body portion, an actuator disposed between the nose member and the wedge member, for translation of the wedge member along a longitudinal axis of the implant, wherein a series of dovetail grooves connect the upper body portion, the lower body portion, the wedge member, and the nose member together. and translation of the wedge member along the longitudinal axis of the implant displaces the upper body portion and the lower body portion away from each other. thereby expanding the intervertebral implant.

In one embodiment, there is provided an expandable intervertebral implant comprising an upper body portion. a lower body portion opposite the upper body portion, a nose member having a tapered distal end and a proximal end opposite the distal end, a wedge member connecting the upper body portion to the lower body portion, and comprising a first wedge and a second wedge connected together, and an actuator disposed between the nose member and the wedge member, for translation of the wedge member along a longitudinal axis of the implant. A back side of the second wedge comprises the posterior end of the implant and comprises an entire height of the implant. Translation of the wedge member along the longitudinal axis of the implant displaces the upper body portion and the lower body portion away from each other, thereby expanding the intervertebral implant.

In one embodiment, there is provided an expandable intervertebral implant comprising an upper body portion, a lower body portion opposite the upper body portion, a nose member having a tapered distal end and a proximal end opposite the distal end, a wedge member connecting the upper body portion to the lower body portion, and comprising a first wedge and a second wedge connected together, and an actuator disposed between the nose member and the wedge member, for translation of the wedge member along a longitudinal axis of the implant. The nose member connects to the upper body portion and the lower body portion by a pair of dovetail grooves on an external surface of the nose member. Translation of the wedge member along the longitudinal axis of the implant displaces the upper body portion and the lower body portion away from each other, thereby expanding the intervertebral implant.

In one embodiment, there is provided a system for stabilization of vertebra, comprising the expandable implant described above; and an insertion tool which turns the actuator described above and thereby expands the implant.

In one embodiment, there is provided a method for stabilization of vertebra, comprising attaching an insertion tool to the expandable implant described above, inserting the expandable implant into an intervertebral space between adjacent vertebra; and expanding the expandable implant.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawing, wherein:

FIG. 5 is a schematic depiction of the individual components of the implant with attention on the dovetail groove assembly construction;

FIG. 6 is a schematic depicting a graft window in the implant;

FIG. 7 is a schematic depicting counter torque slots of the implant; and

FIG. 8 is a flowchart depicting a method of the invention for stabilization of vertebra.

DETAILED DESCRIPTION OF THE INVENTION

The implants of this invention are designed for spinal fusion procedures to be used with autogenous bone graft in skeletally mature patients. While this invention is not so limited, the implants in one embodiment are intended for use at either one level or two contiguous levels in the lumbar spine, from L2 to S1, for the treatment of degenerative disc disease (DDD) with up to Grade I spondylolisthesis. DDD is defined herein as back pain of discogenic origin with degeneration of the disc confirmed by history and radiographic studies.

Expandable Implant

In one embodiment of the invention, the implants constitute expandable posterior lumbar interbody fusion (PLIF) implant products, although this invention is not limited to this specific target use.

Figure 1:
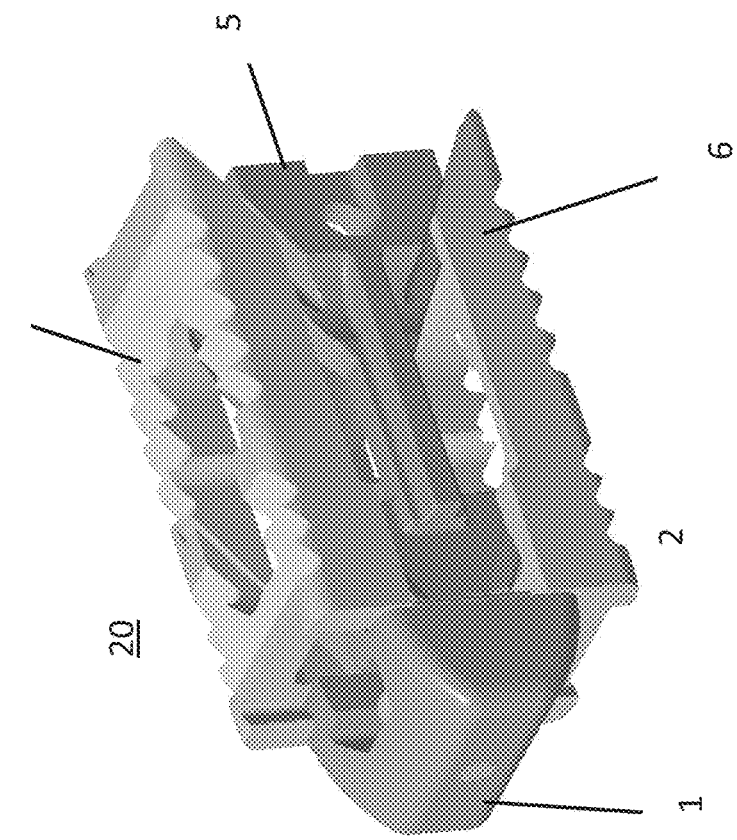
FIG. 1 is a perspective view of the implant device of the invention in a collapsed state.
Figure 2:
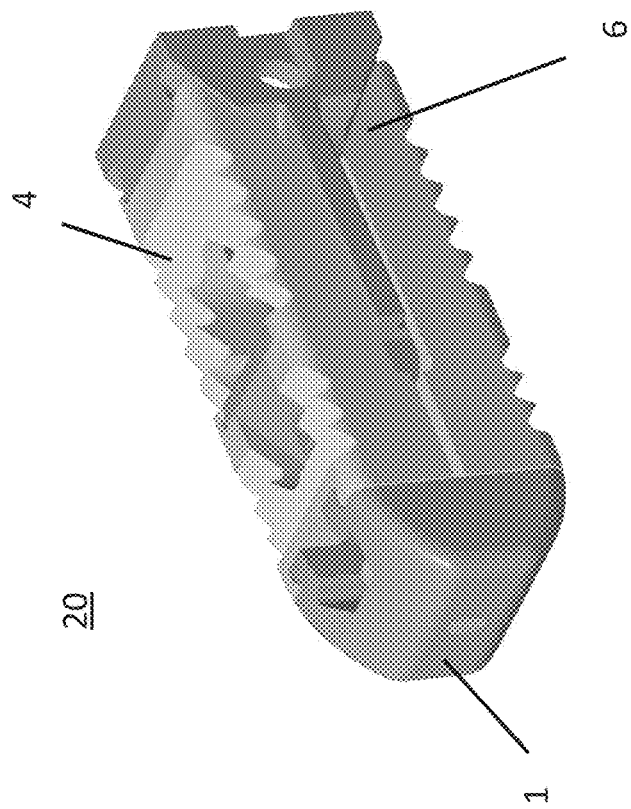
FIG. 2 is a perspective view of the implant device of the invention in an expanded state.

With reference to FIGS. 1 and 2, FIG. 1 is a perspective view of the expandable intervertebral implant 20 in a collapsed state. FIG. 2 is a perspective view of the expandable intervertebral implant 20 in an expanded state. In one embodiment of the invention, the expandable intervertebral implant 20 has a nose member 1 having a tapered distal end and a proximal end opposite the distal end. A pin 2 (not shown in this perspective) is disposed in a center of the nose member 1 and connects to an actuator 3 (not shown in this perspective) for centering the nose member 1 with the actuator 3. The pin 2 maintains a position of the nose member 1 centered to the actuator 3 once the implant has been assembled. An upper body portion 4, a wedge member 5, a lower body portion 6 opposite the upper body portion are shown in FIGS. 1 and 2. The wedge member 5 connects the upper body portion 4 to the lower body portion 5. Translation of the wedge member 5 along the longitudinal axis of the implant, e.g., by turning of the actuator 3, displaces the upper body portion 4 and the lower body portion 6 away from the wedge member 5 and away from each other, thereby expanding the intervertebral implant for example in the cephalad direction denoted in FIG. 3.

Figure 3:
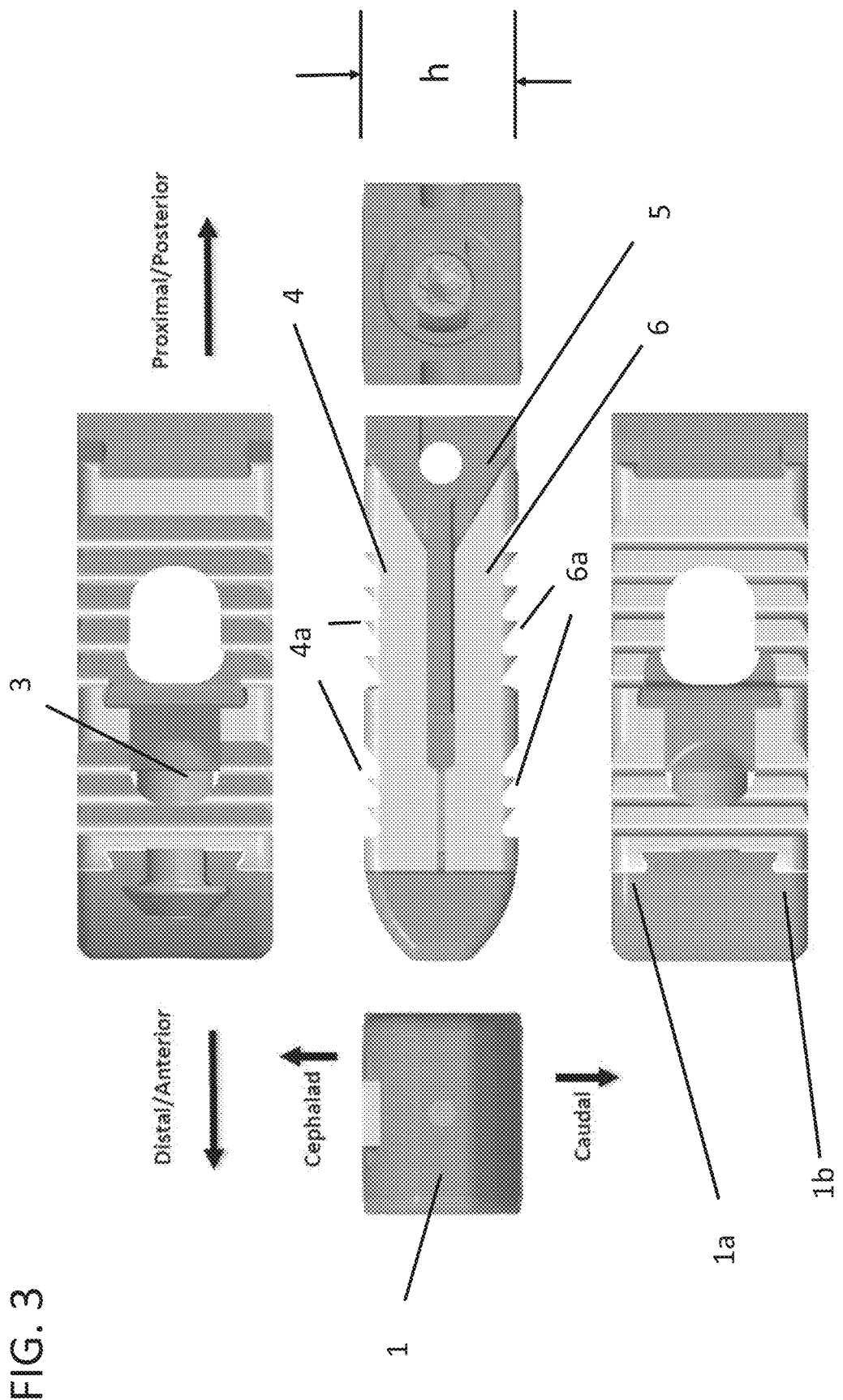
FIG. 3 is a composite drawing showing a top down exploded view, a frontal, side, and rear view. and a bottom view of the implant device of the invention.

FIG. 3 is a composite drawing showing a top down exploded view, a frontal, side, and rear view, and a bottom view of the implant of the invention. As evident from FIG. 3, at least one of the upper body portion 4 and the lower body portion 6 comprises a corrugated surface 4a or 6a for engaging with vertebra. The upper body portion 4 and the lower body portion 6 provide the load bearing surfaces for the intervertebral loads once implant 20 has been implanted and expanded. As evident from FIG. 3, in one embodiment of the invention, the nose member 5 is slidably connected to the upper body portion 4 and is slidably connected to the lower body portion 5 by the exterior dovetail grooves 1a, 1b on nose member 1.

Figure 4:
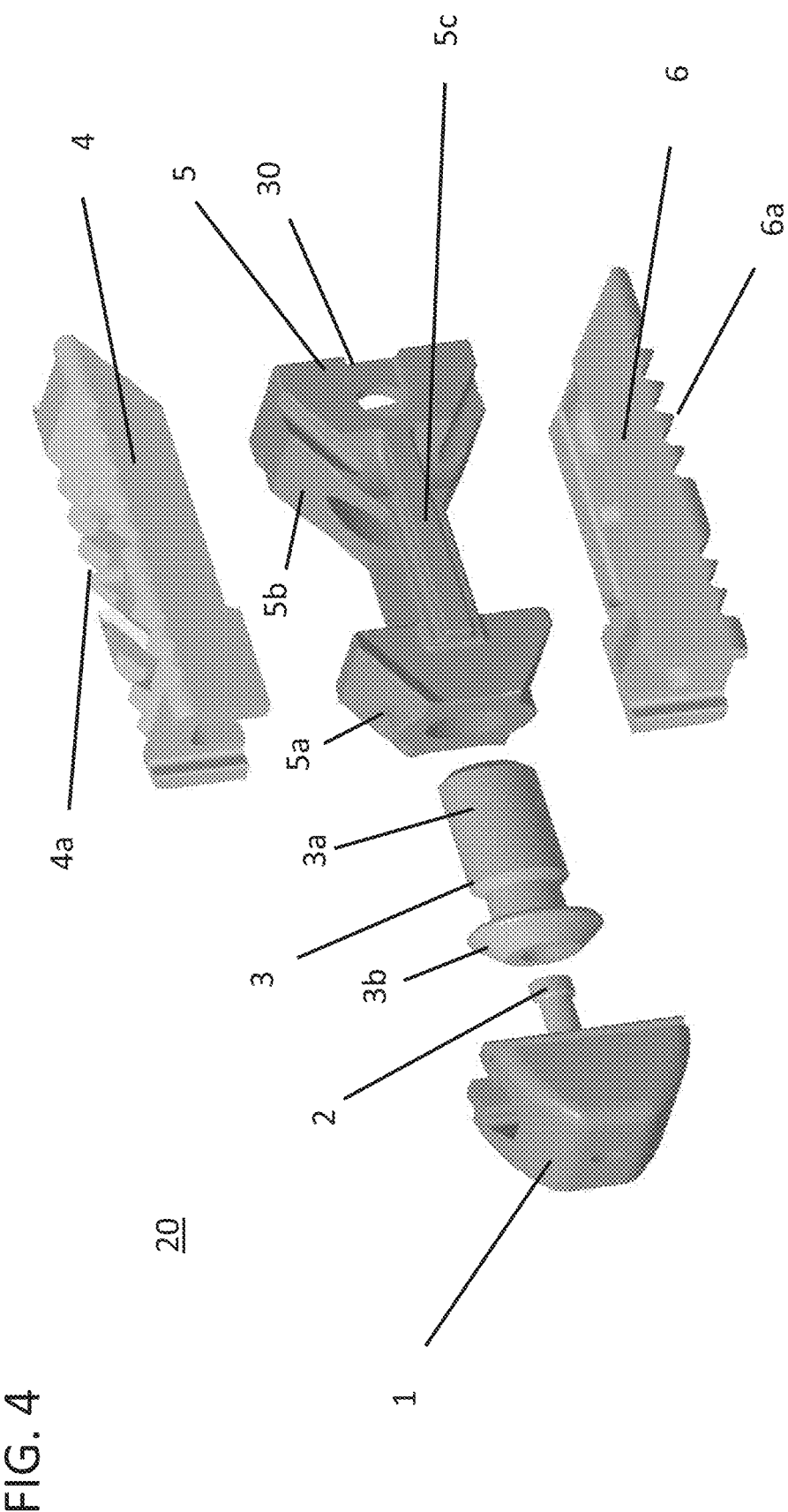
FIG. 4 is a schematic depiction of the individual components of the implant device. showing the relative positions of those components.

FIG. 4 is a schematic depiction of the individual components of the implant 20, showing the relative positions of those components. As evident from FIGS. 3 and 4, actuator 3 is disposed between nose member 1 and wedge member 5. In one embodiment of the invention, the wedge member comprises a first wedge 5a and a second wedge 5b connected together by one or more rails 5c. With reference to FIG. 4, nose member 1 centers by way of pin 2 and retains the head of actuator 3 during expansion of implant 20.

In one embodiment of the invention, the actuator is disposed closer to the nose member than to a posterior of the implant. In general, the inventive implant expands by utilizing actuator 3 which is connected by a threaded connection to wedge member 5, which contains for example a pair of wedges 5a, 5b. When rotated, actuator 3 pulls the wedges (as a set) closer to the nose member 1 of implant 20 and, in turn, drives the upper and lower body portions 4, 6 away from the centerline of implant 20. In other words, with actuator 3 being threadably connected to wedge member 5, rotating actuator 3 translates the wedge member 5 along the longitudinal axis of implant 20. Actuator 3 in one embodiment has a threaded outside surface 3a with a head 3b of the actuator, opposite the wedge member 5, closer to the nose member 1 than to the posterior of implant 20. In one embodiment, actuator 3 and wedge member 5 have respectively male and female threads to thereby advance wedge member 5 when the actuator 3 is turned.

In one embodiment of the invention, the implants comprise low profile implants with a minimal insertion height h for insertion into a collapsed intervertebral disc space. In this aspect of the invention, the height of the implant is that of the wedge member height, as seen in FIG. 3, which constitutes the maximum expansion distance. Accordingly, in this aspect of the invention, back side of the second wedge comprises the posterior end of implant 20 and comprises an entire height of the implant. Once inserted (facilitated by its low profile in this embodiment), implant 20 can expand for example in the cephalad-caudal direction(s) to facilitate disc height restoration.

FIG. 5 is a schematic depiction of the individual components of the implant 20 with attention on the dovetail groove assembly construction. As seen in FIG. 5, nose member 1 uses dovetail grooves 24 to slidably connect and guide expansion of the upper and lower body portions 4, 6 and restrain any anterior-posterior movement of the upper and lower body portions 4, 6. Moreover, in one embodiment, dovetail grooves on the wedge member 5 hold and slidably connect the upper body portion 4 and the lower body portion 6 to the wedge member 5. In another embodiment, dovetail grooves hold and slidably connect the upper body portion 4 and the lower body portion 6 to the nose member 1. In another embodiment, a proximal end of nose member 1 comprises a pair of facing dovetail grooves 1a, 1b comprising respective slots to receive therein the head 3a of the actuator 3.

In still another embodiment, a series of dovetail grooves connect the nose member 1, the upper body portion 4, the wedge member 5, and the lower body portion 6 together. In still another embodiment, the nose member 1 slidably connects to the upper body portion 4 and the lower body portion 6 by a set of dovetail groove on an external surface of the nose member 1. In still another embodiment, a set of dovetail grooves on the first wedge 5a and the second wedge 5b slidably connect the wedge member 5 to the upper body portion 4 and/or to the lower body portion 6. In still another embodiment, a first set of dovetail grooves on the nose member 1 fix the nose member 1 to the upper body portion 4 and the lower body portion 6, and a second set of dovetail grooves on the wedge member 5 fix the upper body portion 4 and the lower body portion 6 to the wedge member 5.

FIG. 6 is a schematic depicting a bone graft window 8 in implant 20. As shown in FIG. 6, an opening in at least one of the upper body portion 4 and the lower body portion 6 is provided for bone graft window 8. The graft window is also incorporated into wedge member 5. In one embodiment of the invention, by disposing the actuator mechanism toward the nose of the implant 20, a relatively large graft window 8 is provided for the implant, and graft material can be injected into the implant 20 once inserted and expanded in the patient. The relatively large graft window facilitates the bone growth and fusion process. In one embodiment, the graft opening can range from 25% to 60% of the endplate area (e.g., the area of the upper or lower body portion) depending on the footprint of implant 20. Regardless of the opening size and configuration, in one embodiment, the implant device provides the capability to backfill bone graft material into a graft window passing all the way though the implant 20.

FIG. 7 is a schematic depicting counter torque slots 28 of implant 20 and a through hole 30 in the posterior end of implant 20. The counter torque slots 28 permit an entirety of implant 20 to be rotated, that is implant 20 as a unit is rotatable. The counter torque slots 28 prevent the implant from rotating. or tipping over, during expansion. The counter torque slots 28 stabilize the implant 20 against the torque being applied to the actuator during expansion. The through-hole 30 grants access for the driver to the actuator. The through-hole 30 also represents an opening for the insertion of bone graft material. In one embodiment of the invention, the wedge member 5 comprises a first wedge 5a and a second wedge 5b connected together by a pair of rails 5c. A through-hole in the first wedge 5a, a second through-hole in the second wedge 5b, and a spacing between the rails 5c comprise a passageway for an insertion tool to connect to and turn actuator 3, and a passageway for bone graft material insertion.

In one embodiment of the invention, there is provided a system for stabilization of vertebra. This system utilizes any of the expandable implants described above; and an insertion tool which turns the actuator described above and thereby expands the implant. For example, actuator 3 shown above can be rotated by a T-7 hexalobular driver fitting the corresponding nut head 32 shown in FIG. 7. Accordingly, in one embodiment, the insertion tool engages the counter torque slots to 1) provide a counter torque during expansion and 2) retain the implant 20 to an inserter supplying bone graft material during the procedure. The bone graft inserter can be cannulated. In one embodiment, the above-noted T-7 driver is placed through the center of the bone graft inserter and engages the actuator. Bone graft material is then pushed through the inserter into implant 20 after implant 20 has been expanded.

In one embodiment, there is provided a method for stabilization of vertebra. FIG. 8 is a flowchart depicting this method. This method at 1001 attaches an insertion tool to any of the expandable implants described above. At 1003, the method inserts one (or more) of the expandable implants into an intervertebral space between adjacent vertebra; and at 1005 expands the expandable implant.

After the expandable implant has been expanded, at 1007, the insertion tool may be removed (e.g., may be pulled from through hole 30 in the posterior end of implant 20. At 1009, bone graft material may then be inserted into the expanded implant filling the graft window 8 in situ. As noted above, the insertion of bone graft material promotes increased fusion.

This invention is not limited to a specific type of bone graft material. In general, a variety of bone graft materials are known and suitable for this invention. These typically comprise calcium phosphate-based or gel-based materials. Polymer-based bone graft substitutes containing (or not containing) collagen can be used. Ceramic bone graft substitutes can be used. In one embodiment, the implantable bone graft material comprises a composite of a ceramic and a polymer. The ceramic and the polymer can be present at a weight ratio ranging from about 10:1 ceramic to polymer to about 2:1 ceramic to polymer. Alternatively, the weight ratio of the ceramic to the polymer can range from about 2:1 (about 66% ceramic to about 33% polymer), from about 3:1 (about 75% ceramic to about 25% polymer). from about 4:1 (about 80% ceramic to about 20% polymer). from about 9:1 (about 90% ceramic to about 10% polymer), from about 10:1 (about 99% ceramic to about 1% polymer). Other bone graft materials besides those specifically listed above can be used.

This invention is also not limited to the type of material that the implant is made of. The implants of this invention can be made of any material appropriate for human implantation and having the mechanical properties sufficient to be utilized for the intended purpose of spinal fusion, including various metals such as cobalt chrome, stainless steel or titanium including its alloys, various plastics including those which are bio-absorbable, and various ceramics or combination sufficient for the intended purpose. Further, the implants of this invention may be made of a solid material, a mesh-like material, a porous material and may comprise, wholly or in part, materials capable of directly participating in the spinal fusion process, or be loaded with, composed of, treated of coated with chemical substances such as bone. morphogenic proteins. hydroxyapatite in any of its forms, and osteogenic proteins, to make them bioactive for the purpose of stimulating spinal fusion. The implants of this invention may be wholly or in part bioabsorbable. Other materials for the implant device besides those specifically listed above can be used.

This invention is also not limited to the methods by which the implants are made. The individual components can be machined from solid stock pieces. Molding can be used to make the individual components. In this case, machining to final dimensions may or may not be in order. The surfaces once properly dimensioned can be coated with a variety of biocompatible coatings and/or surface treatments. Various coatings include for example calcium phosphate ceramics, such as tricalcium phosphate (TCP) and hydroxyapatite (HA), and hydroxyapatite (a naturally occurring material in bone). Moreover. If the implant is not made of bone, surfaces of the implant that contact bone may be treated to promote fusion of the implant to the bone. Treatment may include. but is not limited to, applying a hydroxyapatite coating on contact surfaces, spraying a titanium plasma on contact surfaces, and/or texturing the contact surfaces by scoring. peening. implanting particles in the surfaces, or otherwise roughening the surfaces of the implant.

In some embodiments. any of the implants and instruments described above (such as the insertion tool) can be used with additional implants and instruments. In some embodiments, the implants and instruments can be used with stabilization members, such as plates, screws. and rods. In addition, a multi-level construct can be formed, wherein any one or more of the implants 20 described above can be used on one level, while a similar or different implant (e.g., fusion or prosthetic) can be used on a different level.

Numerous modifications and variations of the present invention are possible in light of the above teachings. It is therefore to be understood that within the scope of the appended claims, the invention may be practiced otherwise than as specifically described herein.

The invention claimed is:

1. An expandable intervertebral implant comprising:
an upper body portion;
a lower body portion opposite the upper body portion;

a wedge member connecting the upper body portion to the lower body portion;

a graft window provided in at least one of the upper body portion and the lower body portion and incorporated in the wedge member;

a nose member having a distal end and a proximal end opposite the distal end, the nose member slidably connected to the upper body portion and the lower body portion;

an actuator for driving the wedge member, wherein the actuator is interior to the wedge member and a proximal-side end of the actuator is disposed a) inside of the graft window and b) closer to the nose member than a proximal side of the implant opposite the nose member;

a through-hole in the wedge member at the proximal side of the implant for access to a head of the actuator and the graft window, wherein translation of the wedge member along the longitudinal axis of the implant displaces the upper body portion and the lower body portion away from each other, thereby expanding the intervertebral implant.

2. The implant of claim 1, further comprising an opening in at least one of the upper body portion and the lower body portion configured to receive bone graft material.

3. The implant of claim 1, wherein at least one of the upper body portion and the lower body portion comprises a corrugated surface for engaging with vertebra.

4. The implant of claim 1, wherein the actuator is threadably connected to the wedge member such that rotating the actuator translates the wedge member along the longitudinal axis.

5. The implant of claim 1, wherein the wedge member comprises a first wedge and a second wedge connected together by a rail.

6. The implant of claim 1, wherein dovetail grooves on the wedge member hold and slidably connect the upper body portion and the lower body portion to the wedge member.

7. The implant of claim 1, wherein dovetail grooves hold and slidably connect the upper body portion and the lower body portion to the nose member.

8. The implant of claim 1, wherein the proximal-side end of the actuator is configured to connect with an insertion tool for insertion of the implant between vertebrae.

9. The implant of claim 1, wherein the actuator by turning advances the wedge member toward the nose member and expands the implant.

10. The implant of claim 9, wherein the actuator and the wedge member have respective male and female threads configured such that, when the actuator is turned, the wedge member is thereby advanced.

11. The implant of claim 1, further comprising: a first set of dovetail grooves on the nose member which fix the nose member to the upper body portion and the lower body portion, and a second set of dovetail grooves on the wedge member which fix the upper body portion and the lower body portion to the wedge member.

12. The implant of claim 1, wherein the proximal end of the nose member comprises a pair of facing dovetail grooves configured to slidably connect and fix the nose member to the upper body portion and the lower body portion, and wherein a slot is configured to receive the first side of the actuator therein.

13. The implant of claim 1, wherein the nose member slidably connects to the upper body portion and the lower body portion by a set of dovetail grooves on an external surface of the nose member.

14. The implant of claim 1, wherein the wedge member comprises a first wedge and a second wedge, and wherein a set of dovetail grooves configured such that the first wedge and the second wedge slidably connect the wedge member to the upper body portion.

15. The implant of claim 1, wherein the wedge member comprises a first wedge and a second wedge, and wherein a set of dovetail grooves configured such that the first wedge and the second wedge slidably connect the wedge member to the lower body portion.

16. The implant of claim 1, further comprising a pin connecting to the actuator.

17. The implant of claim 16, wherein the pin is disposed in a center of the nose member for centering the nose member with respect to the actuator.

18. The implant of claim 16, wherein the pin is configured to maintain the nose member in a position which is centered with respect to the actuator once the implant has been assembled.

19. The implant of claim 1, wherein the actuator on a first side is slidably connected the nose member and on a second side connected to the wedge member.

20. The implant of claim 1, wherein the distal end of the nose member comprises a tapered distal end.

* * * * *